(12) United States Patent
House

(10) Patent No.: US 7,918,831 B2
(45) Date of Patent: Apr. 5, 2011

(54) CATHETER ASSEMBLY HAVING PROTECTIVE SHEATH

(75) Inventor: Jamie Glen House, Colorado Springs, CO (US)

(73) Assignee: Colorado Catheter Company, Inc., Colorado Springs, CO (US)

( * ) Notice: Subject to any disclaimer, the term of this patent is extended or adjusted under 35 U.S.C. 154(b) by 715 days.

(21) Appl. No.: 11/546,338

(22) Filed: Oct. 12, 2006

(65) Prior Publication Data
US 2008/0171998 A1     Jul. 17, 2008

(51) Int. Cl.
*A61M 5/32* (2006.01)
(52) U.S. Cl. ........................................................ 604/192
(58) Field of Classification Search ............... 604/95.04, 604/192, 103.05, 532, 544; 206/364
See application file for complete search history.

(56) References Cited

U.S. PATENT DOCUMENTS

| | | | |
|---|---|---|---|
| 3,750,875 A * | 8/1973 | Juster | 206/364 |
| 3,934,721 A * | 1/1976 | Juster et al. | 206/364 |
| 4,613,659 A * | 9/1986 | Lee et al. | 528/15 |
| 4,622,033 A | 11/1986 | Taniguchi | |
| 4,772,275 A | 9/1988 | Erlich | |
| 4,790,829 A * | 12/1988 | Bowden et al. | 604/244 |
| 4,834,710 A | 5/1989 | Fleck | |
| 4,861,830 A | 8/1989 | Ward | |
| 5,149,326 A | 9/1992 | Woodgrift et al. | |
| 5,173,225 A | 12/1992 | Range et al. | |
| 5,181,913 A | 1/1993 | Erlich | |
| 5,226,530 A * | 7/1993 | Golden | 206/210 |
| 5,293,869 A * | 3/1994 | Edwards et al. | 600/375 |
| 5,681,322 A * | 10/1997 | Hartigan, Jr. | 606/108 |
| 5,779,670 A | 7/1998 | Bidwell et al. | |
| 5,792,114 A | 8/1998 | Fiore | |
| 5,895,374 A | 4/1999 | Rodsten | |
| 5,951,497 A * | 9/1999 | Wallace et al. | 600/587 |
| 6,010,453 A | 1/2000 | Fiddian-Green | |
| 6,053,905 A | 4/2000 | Daignault et al. | |
| 6,059,107 A | 5/2000 | Nosted et al. | |
| 6,090,075 A * | 7/2000 | House | 604/172 |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,578,709 B1 | 6/2003 | Kavanagh et al. | |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,736,805 B2 | 5/2004 | Israelsson et al. | |
| 6,796,960 B2 * | 9/2004 | Cioanta et al. | 604/103.01 |
| 6,848,574 B1 | 2/2005 | Israelsson et al. | |
| 7,380,658 B2 * | 6/2008 | Murray et al. | 206/364 |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2003/0018302 A1 | 1/2003 | Kavanagh et al. | |
| 2003/0194520 A1* | 10/2003 | Simhambhatla | 428/35.7 |
| 2004/0074794 A1 | 4/2004 | Conway et al. | |
| 2004/0153051 A1 | 8/2004 | Israelsson et al. | |

(Continued)

*Primary Examiner* — Nicholas D Lucchesi
*Assistant Examiner* — Diva Ranade
(74) *Attorney, Agent, or Firm* — Moazzam & Associates, LLC

(57) ABSTRACT

Devices and methods are disclosed for a catheterization process, particularly useful for self-performed catheterizations. A catheter is enclosed in a sheath made from a gas-permeable material. This sheath maximizes gas permeability to prevent air build-up at the distal end of the sheath, resulting in easy self-catheterization for even those with limited manual dexterity.

12 Claims, 4 Drawing Sheets

U.S. PATENT DOCUMENTS

| | | |
|---|---|---|
| 2004/0256264 A1 | 12/2004 | Israelsson et al. |
| 2005/0015076 A1 | 1/2005 | Giebmeyer et al. |
| 2005/0109648 A1 | 5/2005 | Kerzman et al. |
| 2005/0137582 A1 | 6/2005 | Kull-Osterlin et al. |
| 2006/0003439 A1* | 1/2006 | Ismagilov et al. ......... 435/287.2 |
| 2006/0025753 A1 | 2/2006 | Kubalak et al. |

* cited by examiner

CATHETER ASSEMBLY HAVING PROTECTIVE SHEATH

BACKGROUND OF THE INVENTION

1. Field of the Invention

The present invention relates generally to catheter devices. More particularly, the present invention relates to urinary catheters having protective sheaths.

2. Background of the Invention

It has become relatively commonplace for the occasional, intermittent or periodic catheterization of an individual's urinary bladder to be employed, as opposed to placement and maintenance of an indwelling catheter that continuously drains urine from the bladder. Short-term or repeated catheterization is appropriate, or even required, for many persons who are in a hospital setting, a nursing home, doctor's office, rehabilitation facility, or in the home. For example, a patient is sometimes catheterized to treat such conditions as urinary retention, the inability to evacuate urine, or for the purpose of obtaining a sterile urine specimen from a patient in a doctor's office or for hospitalized patients.

The need for intermittent catheterization of an individual sometimes arises due to problems typically associated with long-term use of indwelling catheters, such as infections, urethral damage, and bladder damage. Long-term use of an indwelling catheter is also a risk factor for bladder cancer. This is often the case for persons having a neurogenic urinary condition, such as in a spinal cord injury, multiple sclerosis, stroke, trauma, or other brain injury. Conditions that interfere with the individual's ability to voluntarily void the bladder may also arise post-surgically or as a result of benign prostatic hypertrophy or diabetes. Many of the affected individuals are capable of, and would prefer to perform self-catheterization. For many, the level of risk and discomfort of repeated catheterizations carried out over the course of a day (at 3-6 hour intervals, for example) are offset by the accompanying convenience, privacy, or self-reliance that is achieved. Some of the major difficulties that arise in self-catheterization are the lack of satisfactory catheterization kits, the problem of maintaining the required level of sterility during the procedure, and the difficulty of sometimes performing the procedure under conditions of restricted space and privacy.

In assisted, or non self-catheterizations, it is common practice in hospitals to employ a catheterization tray, which typically includes a sterile drape, gloves, a conventional catheter, antiseptic solution, swabs, lubricant, forceps, underpad, and a urine collection container. Assisted catheterization is usually performed with the patient in a supine position. Maintaining a sterile field during the procedure can still be a problem, however, and the "cath tray" procedure is impractical for use with some individuals and situations today.

Many individuals with spinal cord injuries or other neurological diseases routinely perform intermittent catheterization several times a day using conventional catheters or kits and "clean technique." Clean technique typically means that the urethral area is initially swabbed with antiseptic, and efforts are made to avoid contamination of the catheter during the procedure. The user's hands and catheter are not sterile and a sterile field is not maintained. Clean technique is used instead of sterile technique, generally, for two reasons. First, it is very difficult, if not impossible, for individuals who are performing self-catheterization to adhere strictly to sterile technique. Secondly, these individuals are required to catheterize themselves between 3 and 6 times a day, and the cost of a new sterile catheter and the accessories required to perform sterile catheterization becomes excessively expensive for some users. Sometimes an individual will reuse a "cleaned" catheter. As a result, the use of "clean technique" will many times result in contamination and subsequent infection of the urinary tract, causing significant morbidity and cost to the patient and society.

To maintain sterility many catheters are surrounded by sheaths. The user then holds the sheath while pulling the catheter through, avoiding direct contact with the catheter before and during insertion. While the user is pulling the catheter through the sheath, the sheath can tend to bunch up at the proximal end. Any excess air is then forced to the distal end. Towards the end of the insertion, the air can build up at the distal end inflating the sheath to a maximum, which makes it difficult to complete the insertion process. Completion can be particularly difficult for those with limited manual dexterity.

SUMMARY OF THE INVENTION

The present invention provides a catheter with a sheath that has the qualities that relieve these difficulties associated with self-catheterizations. A catheter using a sheath made from a gas-permeable, yet liquid-impermeable, material will allow excess air inside the catheter to leak through the sheath without compromising the integrity, and thus the sterility, of the sheath, relieving the build-up of air at the distal end of the sheath. This will allow even users with low manual dexterity to complete the self-catheterization process efficiently, and with ease.

Furthermore, the present invention can include components that further ease the catheterization process. Particular exemplary components include lubrication so the catheter slides smoothly down the urinary tract, and a guiding tip, which may also have a lubricant reservoir, to give the user something solid to line up the catheter to the urethra. Also, a hydrophilic coating is used on the catheter of certain embodiments to hold the lubricant onto the catheter while in the urinary tract.

An exemplary embodiment of the present invention is a sheath which is made from a silicon-based organic polymer. This sheath is made from low-density polydimethylsiloxane. This material has a gas-permeability much greater than that of conventional polyolefins allowing air to flow through four-hundred times faster.

Yet another embodiment of the present invention is a sheath made from a microporous polyolefin. This material is characterized with the unique property of containing tortuous sub micron-size passageways extending from one surface side to the other. This permits gases and vapors to permeate and prohibits the penetration of sample particles.

DETAILED DESCRIPTION OF THE INVENTION

Figure 1A:
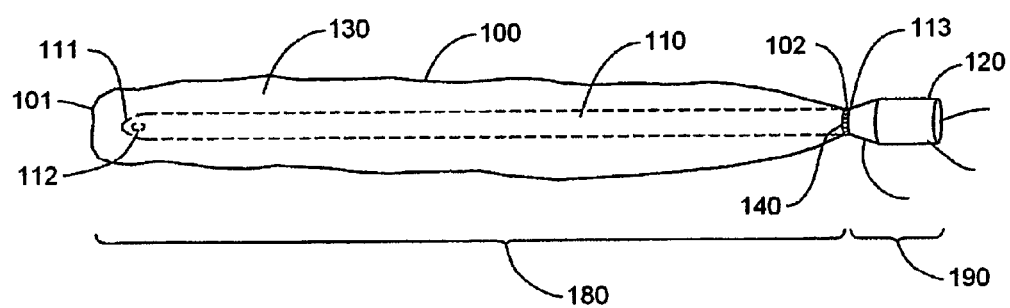
FIG. 1A shows an external perspective view of a catheter surrounded by a sheath according to an exemplary embodiment of a conventional assembly.
Figure 1B:
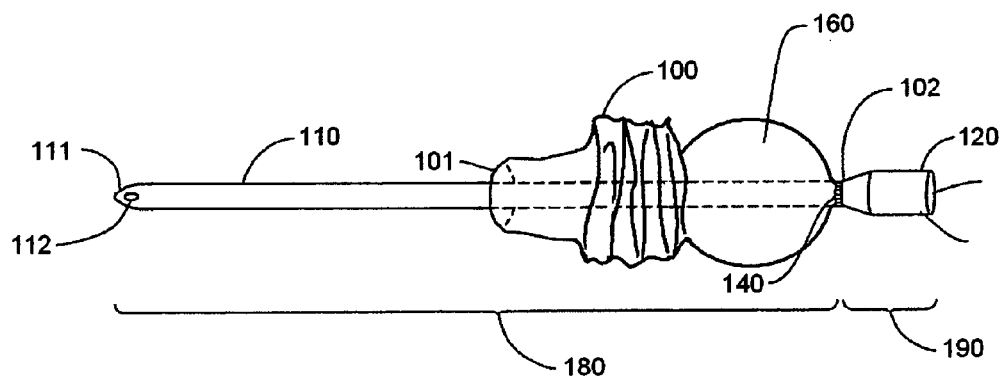
FIG. 1B shows an external perspective view of a catheter surrounded by a sheath with the sheath pulled back to expose the catheter and showing an air pocket created.

The present invention includes devices and methods for urinary catheterization for patients who want to self-catheterize in a sterilie, safe, and efficient manner. In order to achieve the level of sterility required to avoid infection, a sheath 100 is used to cover the portion of the catheter that is insertable into the urethra 180, as shown in FIGS. 1A and 1B. The sheath covers the catheter 110 from time of manufacture and storage until it is fully inserted. The user pulls the catheter 110 through the sheath 100 without touching the catheter 110 itself. As the user pulls the catheter 110 through the sheath 100, excess air builds up 160 at the distal end of the sheath 102. This excess air 160 needs to be released from inside the sheath 100 to the outside atmosphere to allow further advancement of the catheter 110. The sheath 100 in the present invention is made from a gas-permeable material, which allows air to flow through the sheath 100 preventing build-up 160 towards the distal end without compromising sterility.

"Gas-permeable," as defined in the present disclosure, is the ability for air to penetrate through a medium. An exemplary embodiment of the present invention features a material in which gas can penetrate fast enough therethrough such that change in the air-pocketing of the media is noticeable by the human eye. The air inside the sheath is put under pressure when the sheath bunches up at the proximal end during use. While under pressure, the exemplary sheath transfers enough air to the outside atmosphere for the user to notice a reduction in the size of the sheath around the pressurized area.

One group of materials that has this gas-permeability is silicon-based organic polymers, also known as silicon oils. They are flexible, strong, and can retain their strength through a wide range of temperatures. They are very resistant to chemicals and ultraviolet rays, and are gas permeable. Silicon-based organic polymers are liquid-impermeable and do not allow bacteria or other harmful substances to pass, making them useful in medical applications such as the present invention.

An exemplary silicon-based organic polymer for use in the present invention is polydimethylsiloxane, also known as dimethicone or its trade name, SILICON ELASTOMER. Its density ranges from 1.1 to 1.5 g/cm$^3$. Its density is proportional to its gas-permeability, so a less dense version of polydimethylsiloxane, 1.1 to 1.3 g/cm$^3$, is useful in certain exemplary embodiments.

Another group of materials suitable for the present invention is microporous polyolefins. Unlike regular polyolefins, these microporous polyolefins have tortuous sub micron-size passageways extending from one surface side to the other. This allows the passage of gas and vapor while prohibiting the passage of particles and liquids. The microporous polyolefin material can be made by taking a microporous polyolefin matrix and sufficiently filling the pores with a moisture-vapor permeable, liquid-impermeable, hydrophilic material to prevent the passage of water and other liquids through the polyolefin material while readily permitting moisture vapor. One example of such a material is presented in U.S. Pat. No. 4,613,544, entitled "Waterproof, moisture-vapor permeable sheet material and method of making the same," issued to Burleigh, which is incorporated by reference herein in its entirety.

An exemplary embodiment of a conventional assembly for a catheter with a sheath is shown in FIG. 1A. The proximal end of the sheath 101 surrounds the proximal tip of the catheter 111 and is closed at the end. The distal end of the sheath 102 is attached near the distal end of the urethra insertable portion of the catheter 180 with plastic or elastomeric ties or bands 140 or heat sealed. Alternately, the distal end of the sheath 102 could be attached to the outlet 120 if the catheter employs one. This outlet 120 could then be used to attach a urine bag or the like.

In order to perform a catheterization using this device, the user must first open the proximal end of the sheath 100, exposing the proximal end of the catheter 111. The user then holds the proximal tip of the catheter 111 with the sheath 100 between the user's hand and the catheter 110 and pulls the sheath 100 with the other hand. As the user pulls the sheath 100, which is attached to the catheter at its distal end 113, the catheter 110 will be pushed through the sheath 100 and into the urethra, causing the sheath 100 to bunch up at the proximal end 101. A gap is shown at the proximal end 101 to show the detail of this end but this gap is not of such size to allow venting into the sheath 100. At the distal end of the sheath 102 the air will build up 160, causing the sheath 100 to expand to a maximum, preventing the catheter 110 from furthering through the sheath. This is illustrated in FIG. 1B.

Figure 2A:
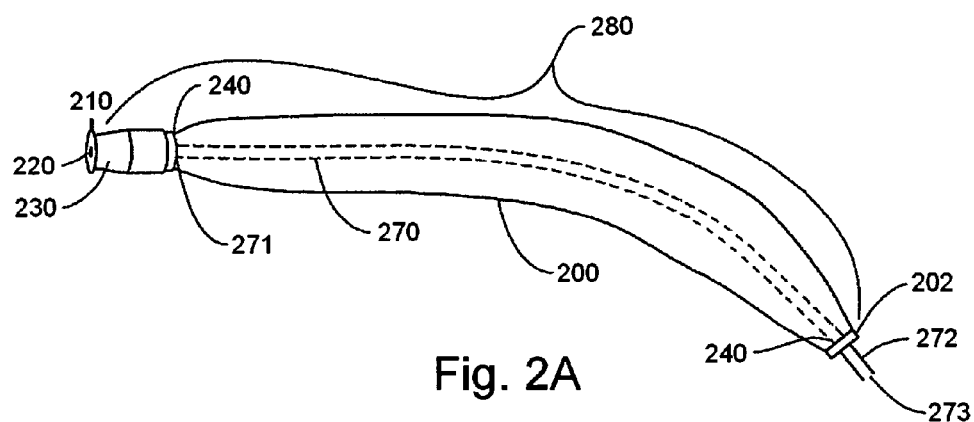
FIG. 2A shows an external perspective view of a catheter surrounded by a sheath attached to a guide tip at the proximal end according to an exemplary embodiment of a conventional assembly.
Figure 2B:
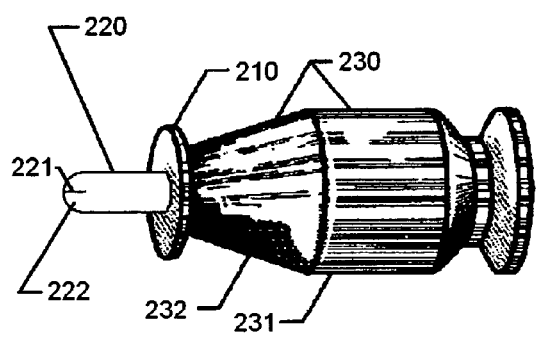
FIG. 2B shows a close-up view of a guiding tip according to an exemplary embodiment of the present invention.
Figure 2C:
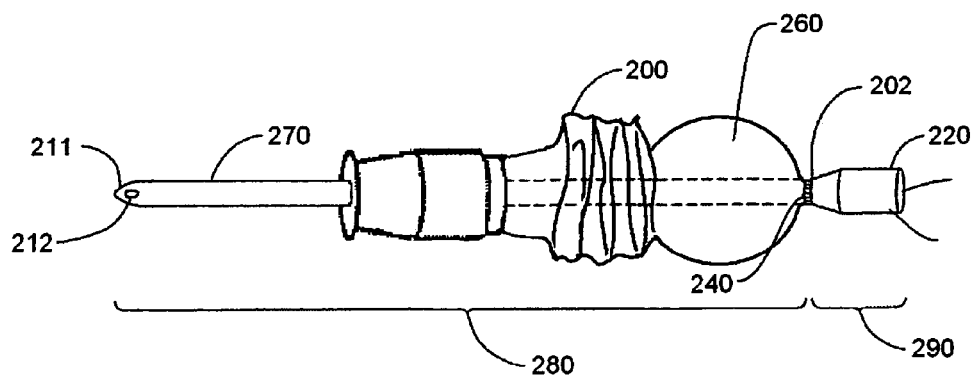
FIG. 2C shows an external perspective view of a catheter surrounded by a sheath attached to a guide tip at the proximal end with the sheath pulled back, forcing the catheter through the guide tip and showing an air pocket created.

FIG. 2A shows an embodiment of a conventional assembly that also has a guiding tip, FIG. 2B. This embodiment, as illustrated in FIG. 2C, is also susceptible to inhibited catheter 270 movement caused by the air build-up 260 at the distal end of the sheath 202.

Figure 3A:
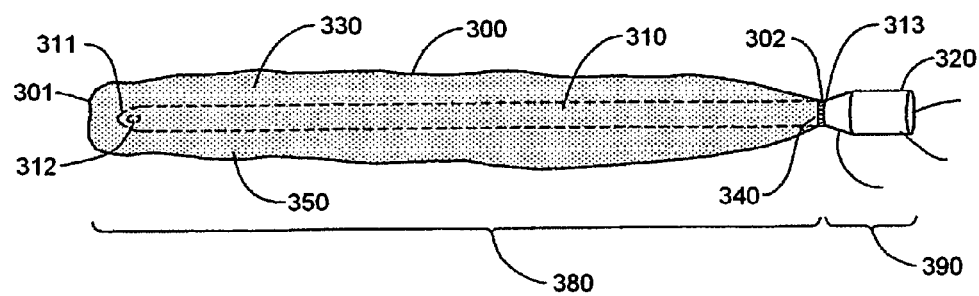
FIG. 3A shows an external perspective view of a catheter surrounded by a gas-permeable sheath according to an exemplary embodiment of the present invention.

In FIG. 3A, there is an exemplary embodiment of the present invention shown, featuring a sheath 300 made from a gas-permeable, liquid-impermeable material 350, such as the materials disclosed above, or similar in function. This material 350 will allow the air built-up inside the sheath to escape to the outside atmosphere 360 at a rate fast enough for the user to complete the catheterization process without undue pause, as illustrated in FIG. 3B.

Figure 3B:
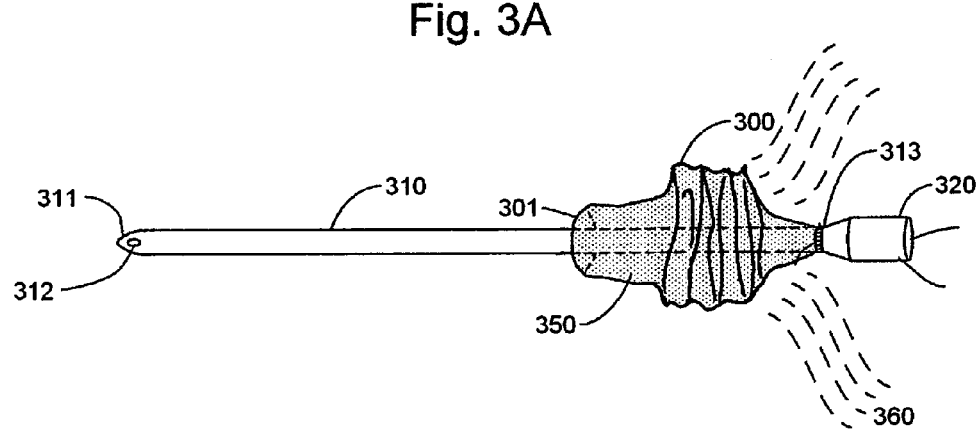
FIG. 3B shows an external perspective view of a catheter surrounded by a gas-permeable sheath with the sheath pulled back to expose the catheter and showing no air pocket.

Referring to FIGS. 3A and 3B, the catheter insertion process continues until the catheter 310 runs all the way through the urethra and into the bladder. Once inside, fluid from the bladder will stream into the catheter through the hole 312 at the proximal tip of the catheter 311. Provided the catheter distal end 313 is lower in altitude than the catheter proximal end 311, fluid will flow through the catheter, out the outlet 320, and into a receptacle. When the bladder has been drained of all fluid the catheter 310 is then pulled out of the urethra by the user, and disposed.

In certain exemplary embodiments, the sheath 300 may be filled with enough lubricant 330 to coat the insertable length of the catheter 380. This will be a water-based lubricant of the type used on rectal thermometers and enemas, such as KY-JELLY®, or the like. As the catheter 310 is pushed through the sheath 300, the lubricant 330 is pushed through as well, lubricating the insertable portion of the catheter 380 on its way into the urethra. The lubricant 330 will ease the process of sliding the catheter 310 into the urethra by reducing the friction between the catheter 310 and the urethra. By reducing the friction the user can insert the catheter 310 faster and with less pain.

Figures 4A, 4B:
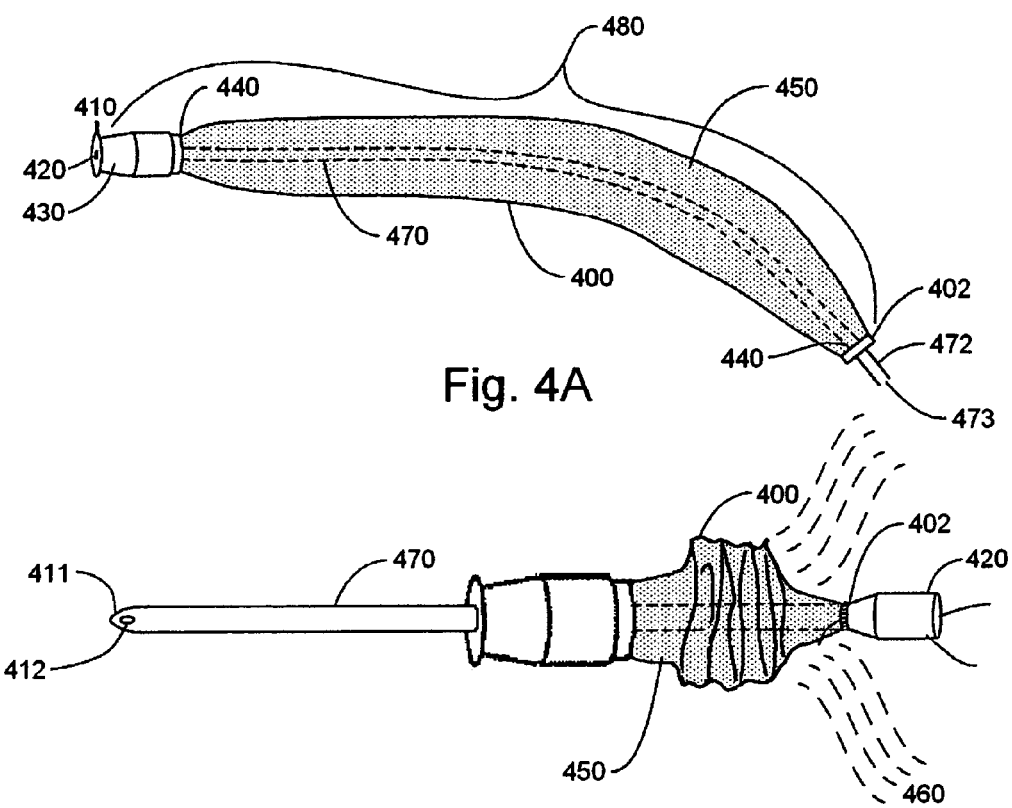
FIG. 4A shows an external perspective view of a catheter surrounded by a gas-permeable sheath attached to a guide tip at the proximal end according to an exemplary embodiment of the present invention.
FIG. 4B shows an external perspective view of a catheter surrounded by a gas-permeable sheath attached to a guide tip at the proximal end with the sheath pulled back, forcing the catheter through the guide tip and showing no air pocket.

In another embodiment shown in FIG. 4A, the catheter 470 has a guiding tip 430 at the proximal end of the catheter 411. The guiding tip 430 helps the user hold the catheter 470 in place while inserting it into the urethra. The guiding tip 430 has a throughbore 420 in the center which the catheter 470 can slide through. In use, FIG. 4B illustrates the sheath's 400 ability to release built-up air to the outside atmosphere 460 even when the assembly includes a guiding tip 430 at the proximal end 411. With no air built-up in the distal end of the sheath, the user can easily push the catheter through the sheath completely.

An exemplary embodiment of the guiding tip 430 is illustrated in FIG. 2B as tip 230. Although described with respect to FIG. 2B, the same guiding tip is applicable to the one shown in FIGS. 4A and 4B. At the proximal end of the guiding tip 230 is a collar 210, with a size of about 10-15 mm, which, during insertion, rests on the outside of the urethra. At the proximal end of the collar 210 is a short tube 220 just wider than the catheter 270. This tube 220 ends in a rounded top with two cuts in the top 221. When the catheter 270 is pushed through the top the tube 220 splits into four tabs 222, allowing the catheter 270 to pass. Towards the distal end of the guiding tip 230 there is also a reservoir portion 230. The distal half of the reservoir is a hollow cylinder 231 while the proximal half is a hollow frustoconical section 232. The reservoir portion 231 contains the same lubricant that is held inside the sheath 200. This makes the guiding tip 230 longer and bulkier, and gives the user more to hold onto while sliding the catheter 270 through. On the outside of the reservoir 231, texture may be added for enhanced gripping. Other embodiments of the guiding tip can be found in U.S. Pat. No. 6,090,075, entitled "Disposable urinary catheterization assembly", issued to House, which is incorporated by reference herein in its entirety.

In other embodiments the catheter may be coated with a hydrophilic substance, commonly known as hydrogel, particularly useful on indwelling catheters. This hydrophilic coating helps the catheter to hold the lubricant on its surface while inside the urinary tract. One such hydrophilic substance that can be used is agarose, known also under its trade name BIOGEL A.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A catheter assembly comprising:
   a catheter; and
   a sheath, made of a liquid-impermeable material that is sterile or able to withstand sterility treatment, impermeable to bacteria and other contaminants, and gas-permeable, surrounding and enclosing at least an insertable portion of the catheter, the sheath composed of a microporous polyolefin material, the microporous polyolefin material made by taking a microporous polyolefin matrix and filling pores of the microporous polyolefin matrix with a moisture-vapor permeable, liquid-impermeable, hydrophilic material to prevent the passage of liquids through the microporous polyolefin material while readily permitting passage of moisture vapor, the sheath preventing air buildup at a distal end of the sheath as the sheath bunches up during insertion of the catheter, the sheath preventing the air buildup by transferring air through a wall of the sheath to an outside atmosphere, wherein a gap in the sheath at the proximal end created during insertion is not of such size to allow venting into the sheath.

2. The catheter assembly of claim 1, wherein the sheath has a gas-permeability great enough to, while under pressure, relieve air from inside the sheath so that the sheath decreases in volume at a rate visible to the naked eye.

3. The catheter assembly of claim 1, wherein the polyolefin is polypropylene.

4. The catheter assembly of claim 3, wherein the polypropylene density is 0.87 to 0.9 g/cm.sup.3.

5. A urinary catheter assembly comprising:
   a urinary catheter; and
   a sheath, made of a liquid-impermeable material that is sterile or able to withstand sterility treatment, impermeable to bacteria and other contaminants, and gas-permeable, surrounding and enclosing at least an insertable portion of the catheter, the sheath composed of a microporous polyolefin material, the microporous polyolefin material made by taking a microporous polyolefin matrix and filling pores of the microporous polyolefin matrix with a moisture-vapor permeable, liquid-impermeable, hydrophilic material to prevent the passage of liquids through the microporous polyolefin material while readily permitting passage of moisture vapor, the sheath preventing air buildup at a distal end of the sheath as the sheath bunches up during insertion of the catheter, the sheath preventing the air buildup by transferring air through a wall of the sheath to an outside atmosphere, wherein a gap in the sheath at the proximal end created during insertion is not of such size to allow venting into the sheath.

6. The urinary catheter assembly of claim 5, wherein the sheath has a gas-permeability great enough to, while under pressure, relieve air from inside the sheath so that the sheath decreases in volume at a rate visible to the naked eye.

7. The urinary catheter assembly of claim 5, wherein the polyolefin is polypropylene.

8. The urinary catheter assembly of claim 7, wherein the polypropylene density is 0.87 to 0.9 g/cm.sup.3.

9. An intermittent urinary catheter assembly comprising:
   a flexible, urinary catheter; and
   a sheath, made of a liquid-impermeable material that is sterile or able to withstand sterility treatment, impermeable to bacteria and other contaminants, and gas-permeable, surrounding and enclosing at least an insertable portion of the catheter, the sheath composed of a microporous polyolefin material, the microporous polyolefin material made by taking a microporous polyolefin matrix and filling pores of the microporous polyolefin matrix with a moisture-vapor permeable, liquid-impermeable, hydrophilic material to prevent the passage of liquids through the microporous polyolefin material while readily permitting passage of moisture vapor, the sheath preventing air buildup at a distal end of the sheath as the sheath bunches up during insertion of the catheter, the sheath preventing the air buildup by transferring air through a wall of the sheath to an outside atmosphere, wherein a gap in the sheath at the proximal end created during insertion is not of such size to allow venting into the sheath.

10. The intermittent urinary catheter assembly in claim 9, wherein the sheath has a gas-permeability great enough to, while under pressure, relieve air from inside the sheath so that the sheath decreases in volume at a rate visible to the naked eye.

11. The intermittent urinary catheter assembly in claim 9, wherein the polyolefin is polypropylene.

12. The intermittent urinary catheter assembly in claim 11, wherein the polypropylene density is 0.87 to 0.9 g/cm$^3$.

* * * * *